(12) United States Patent
Poigny et al.

(10) Patent No.: US 9,422,261 B2
(45) Date of Patent: Aug. 23, 2016

(54) HETEROCYCLIC RESORCINOL DERIVATIVES, PREPARATION OF SAME AND COSMETIC USES THEREOF

(75) Inventors: Stéphane Poigny, Saubens (FR); Françoise Belaubre, Villeneuve Tolosane (FR)

(73) Assignee: PIERRE FABRE DERMO-COSMETIQUE, Boulogne-Billancourt (FR)

( * ) Notice: Subject to any disclaimer, the term of this patent is extended or adjusted under 35 U.S.C. 154(b) by 309 days.

(21) Appl. No.: 13/983,742

(22) PCT Filed: Feb. 7, 2012

(86) PCT No.: PCT/EP2012/051998
§ 371 (c)(1),
(2), (4) Date: Oct. 3, 2013

(87) PCT Pub. No.: WO2012/107421
PCT Pub. Date: Aug. 16, 2012

(65) Prior Publication Data
US 2014/0050683 A1    Feb. 20, 2014

(30) Foreign Application Priority Data

Feb. 7, 2011   (FR) ..................................... 11 50957

(51) Int. Cl.
| | |
|---|---|
| *A61Q 5/08* | (2006.01) |
| *C07D 333/16* | (2006.01) |
| *A61K 8/49* | (2006.01) |
| *A61Q 17/00* | (2006.01) |
| *A61Q 19/02* | (2006.01) |
| *A61Q 19/08* | (2006.01) |
| *C07D 213/30* | (2006.01) |
| *C07D 277/24* | (2006.01) |

(52) U.S. Cl.
CPC ................ *C07D 333/16* (2013.01); *A61K 8/49* (2013.01); *A61K 8/4926* (2013.01); *A61K 8/4986* (2013.01); *A61Q 5/08* (2013.01); *A61Q 17/005* (2013.01); *A61Q 19/02* (2013.01); *A61Q 19/08* (2013.01); *C07D 213/30* (2013.01); *C07D 277/24* (2013.01)

(58) Field of Classification Search
CPC ....................................................... A61Q 5/08
See application file for complete search history.

(56) References Cited

U.S. PATENT DOCUMENTS

| | | | |
|---|---|---|---|
| 2007/0098655 | A1 | 5/2007 | Schmaus et al. |
| 2009/0074691 | A1* | 3/2009 | Gupta ............................. 424/62 |
| 2010/0016347 | A1 | 1/2010 | Nandy et al. |

FOREIGN PATENT DOCUMENTS

WO   WO 2010/011630 A1   1/2010

OTHER PUBLICATIONS

International Search Report for PCT/EP2012/051998 dated Apr. 5, 2012.

* cited by examiner

*Primary Examiner* — Benjamin Packard
(74) *Attorney, Agent, or Firm* — Birch, Stewart, Kolasch & Birch, LLP

(57) ABSTRACT

The invention relates to a compound of general formula (I)

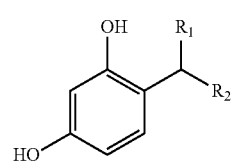

(I)

characterized in that:
R$_1$ is a C$_1$-C$_4$ alkyl group, and
R$_2$ is an optionally substituted nitrogen, sulfur or oxygen containing heteroaromatic ring.

19 Claims, No Drawings

HETEROCYCLIC RESORCINOL DERIVATIVES, PREPARATION OF SAME AND COSMETIC USES THEREOF

The present invention relates to novel resorcinol analogs, uses thereof and methods for preparing same.

The present invention relates to novel resorcinol analogs of the general formula (I):

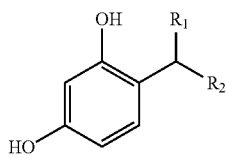
(I)

wherein:
$R_1$ is a $C_1$-$C_4$ alkyl and $R_2$ is a nitrogen-, sulfur- or oxygen-containing heteroaromatic ring.

Resorcinol (or benzene 1,3-diol) of the following formula:

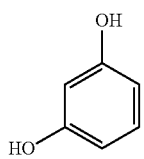

is known for various uses as an antiseptic, but above all as a colorant such as resorcin blue or resorcin green. The latter are used as color changing indicators in certain acid-base titrations.

Resorcinol analogs have been described in the patent application WO 2010/011630 of Unigen Pharmaceuticals Inc. and have a general formula similar to that of the present invention, namely:

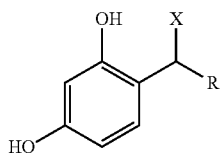

wherein X can be either a hydrogen atom or an —OH radical, and R is an aromatic or heteroaromatic nucleus; the present invention differs by providing derivatives of different chemical formulas.

The problem that the present invention proposes to solve is the inhibition of melanin synthesis, by the inhibition of tyrosinase activity (essential for melanin synthesis), and by the use of these novel resorcinol analogs, with the aim of achieving an effective depigmentation of the skin.

Furthermore, the use of these resorcinol analogs is proposed to fight against aging of the skin by, inter alia, a high antioxidant activity of these compounds.

The epithelium of the skin, formed of the epidermis and the dermis, gives to skin its color principally through special cells called melanocytes. Melanocytes produce melanin, which is composed of several pigments.

Tyrosinase is a limiting enzyme in melanogenesis, whose inhibition leads to depigmentation. It is a member of the family of oxidoreductases.

Tyrosinase has in particular the following functional groups: monophenol monooxygenase (MPMO) and polyphenol oxidase (PPO).

Tyrosinase is synthesized by melanocytes. It is activated during its migration toward keratinocytes via melanosomes. It transforms tyrosine into DOPA and then dopaquinone, which leads to polymerization or production of pigments (see diagram below).

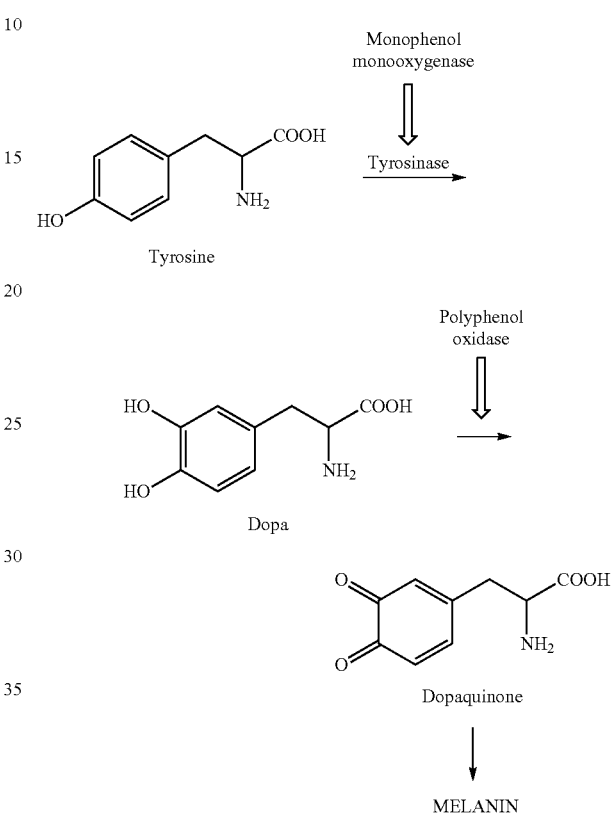

From the point of view of the prior art, the patent application WO 2010/011630 of Unigen Pharmaceuticals Inc. showed that the resorcinol derivatives claimed in this application were endowed with a certain activity of inhibition of tyrosinase activity, of inhibition of melanin production and an ability to whiten the skin.

The inventor of the present invention provides a response to this in terms of effectiveness superior to that described for the claimed compounds of the prior art. At the same time, these compounds prove to be better depigmenting agents.

The present invention thus relates to novel resorcinol analogs of the general formula (I):

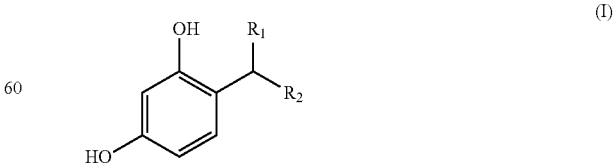
(I)

wherein:
$R_1$ is a $C_1$-$C_4$ alkyl and $R_2$ is a nitrogen-, sulfur- or oxygen-containing heteroaromatic ring, in particular a heteroaromatic single-ring, preferably a heteroaromatic ring with 5 or 6 members, said ring being optionally substituted by a linear or branched $C_1$-$C_4$ alkyl radical, preferably a methyl radical, and having as preferred radicals, the following radicals: $R_1$ is methyl and $R_2$ is selected from 3-pyridyl, 4-pyridyl, 2-furyl, 3-furyl, 2-thiophenyl, 3-thiophenyl, 2-thiazolyl.

In accordance with an embodiment of the invention, the compounds of general formula (I) can be selected from the following:

4-(1-(pyridin-2-yeethyl)benzene-1,3-diol (compound 2);
4-(1-(pyridin-3-yl)ethyl)benzene-1,3-diol (compound 3);
4-(1-(pyridin-4-yl)ethyl)benzene-1,3-diol;
4-(1-(thiophene-2-yl)ethyl)benzene-1,3-diol (compound 1);
4-(1-(thiophene-3-yl)ethyl)benzene-1,3-diol (compound 4);
4-(1-(thiazol-2-yl)ethyl)benzene-1,3-diol (compound 5);
4-(1-(1-methyl-1H-benzo[d]imidazol-2-yl)ethyl)benzene-1,3-diol;
4-(1-(1-methyl-1H-indol-2-yDethyl)benzene-1,3-diol;
4-(1-(benzo[b]thiophene-2-yl)ethyl)benzene-1,3-diol;
4-(1-(thiophene-2-yl)butyl)benzene-1,3-diol (compound 31);
4-(3-methyl-1-(thiophene-2-yl)butyl)benzene-1,3-diol (compound 28).

The invention also relates to the cosmetic use of compounds of formula (I), and in particular the use of same for the depigmentation of the skin, for the implementation of a method of cosmetic treatment of skin aging.

The present invention relates to the cosmetic use of compounds of general formula (I) as an antioxidant active ingredient or a depigmenting active ingredient.

The invention also relates to pharmaceutical or cosmetic compositions including at least one of the compounds of formula (I) in combination with at least one pharmaceutically or cosmetically acceptable excipient.

In the present invention, the term "pharmaceutically or cosmetically acceptable" refers to that which is useful in the preparation of a pharmaceutical or cosmetic composition; is generally safe, nontoxic and neither biologically nor otherwise undesirable; and is acceptable for therapeutic or cosmetic use, in particular by topical application.

The object of the invention relates to a cosmetic composition characterized in that the quantity of the compound of formula (I) varies between 0.01% and 10% by weight, and preferably from 0.1% to 5% by weight, in relation to the total weight of the composition.

The present invention relates to a method of bleaching and/or lightening human skin and/or body hair and/or head hair, which comprises applying on the skin and/or body hair and/or head hair a cosmetic composition containing at least one compound of formula (I).

The present invention relates to a method of cosmetic treatment and/or prevention of skin aging, which comprises applying on the skin a cosmetic composition containing at least one compound of formula (I).

The object of the invention also extends to the method of synthesizing the novel compounds of formula (I).

The present invention will be better understood from the examples given below for the purpose of illustration.

EXAMPLE 1

Synthesis of Compound 1:
4-(1-(thiophene-2-yl)ethyl)benzene-1,3-diol

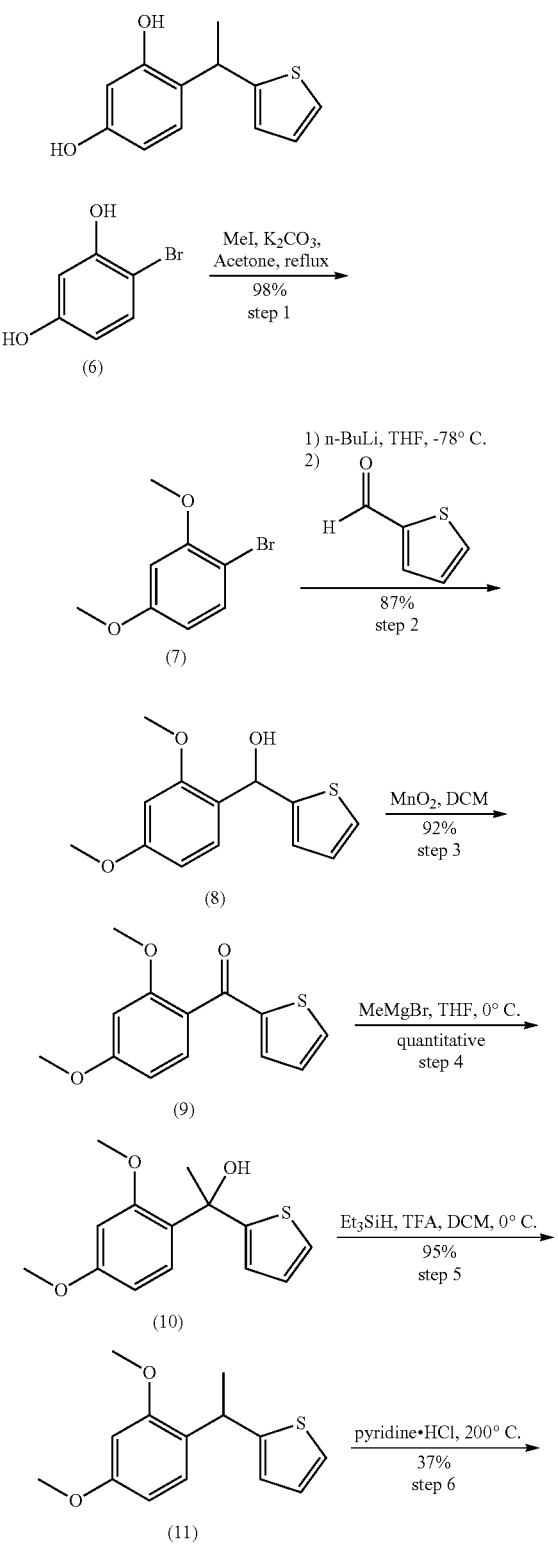

-continued

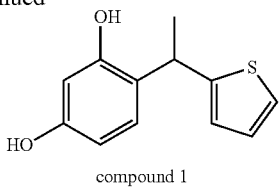

compound 1

Synthesis of Compound (7)

1-bromo-2,4-dimethoxybenzene

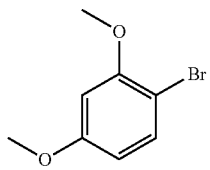

Potassium carbonate (22 g; 158.7 mmol; 3.0 eq) and iodomethane (9.9 ml; 158.7 mmol; 3.0 eq) are added successively to a solution of compound (6) (10 g; 52.9 mmol; 1.0 eq) in 200 ml of acetone. The reaction mixture is stirred at reflux for 20 hours and then evaporated under reduced pressure. The residue obtained is taken up in 200 ml of water and extracted with ethyl acetate (2×200 ml). The organic phases are combined, dried over $MgSO_4$ and then evaporated to lead to compound (7) (11.2 g; 98%) obtained as a yellow oil.

$^1$H NMR (300 MHz, $CDCl_3$): δ: 3.83 (s, 3H); 3.89 (s, 3H); 6.42 (dd, 1H); 6.50 (d, 1H); 7.42 (d, 1H).

Synthesis of Compound (8)

(2,4-dimethoxyphenyl)(thiophene-2-yl)methanol

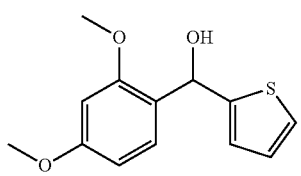

1.6 M solution of n-butyllithium in hexane (9.5 ml; 15.2 mmol; 1.1 eq) is added dropwise to a solution of compound (7) (3 g; 13.8 mmol; 1.0 eq) in 90 ml of anhydrous THF cooled to −78° C. The solution is stirred for 1 hour at −78° C. and then 2-formylthiophene (4.7 ml; 49.5 mmol; 3.6 eq) is added dropwise. The solution is stirred for 3 hours at 78° C., then for 15 hours at room temperature, and then 150 ml of water is added. After extraction with ethyl acetate (2×150 ml), the organic phases are combined, dried over $MgSO_4$ and concentrated under reduced pressure. The oil obtained is purified by chromatography on silica gel (eluent: cyclohexane/ethyl acetate: 10:0 to 8:2) to lead to a mixture of compound (8) and thiophene-2-methanol (3.3 g; 85% by mass of compound (8); 87%) obtained as a yellow oil.

$^1$H NMR (300 MHz, $CD_3COCD_3$): δ: 3.80 (s, 3H); 3.82 (s, 3H); 4.83 (d, 1H); 6.28 (dd, 1H); 6.54 (m, 2H); 6.83 (dd, 1H); 6.89 (dd, 1H); 6.97 (dd, 1H); 7.26 (dd, 1H); 7.43 (d, 1H).

Synthesis of Compound (9)

(2,4-dimethoxyphenyl)(thiophene-2-yl)methanone

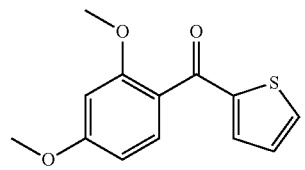

$MnO_2$ (6.0 g; 69.0 mmol; 6.1 eq) is added to a solution of compound (8) (3.3 g (85% by mass); 11.24 mmol; 1.0 eq) in 100 ml of dichloromethane. The reaction mixture is stirred for 2 days at room temperature and then filtered on Celite. The filtrate is concentrated under reduced pressure to lead to a mixture of compound (8) and compound (9). This mixture is reacted under the same conditions for 2 days. After filtration on Celite and evaporation to dryness, the residue is purified by chromatography on silica gel (eluent: cyclohexane/ethyl acetate: 10:0 to 9:1) to lead to compound (9) (2.55 g; 92%) obtained as a yellow oil.

$^1$H NMR (300 MHz, $CD_3COCD_3$): δ: 3.80 (s, 3H); 3.90 (s, 3H); 6.65 (dd, 1H); 6.70 (d, 1H); 7.19 (dd, 1H); 7.37 (d, 1H); 7.49 (dd, 1H); 7.90 (dd, 1H).

Synthesis of Compound (10)

1-(2,4-dimethoxyphenyl)-1-(thiophene-2-yl)ethanol

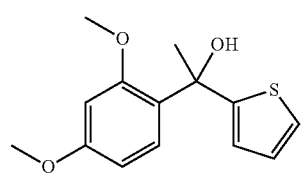 [SMILES: COc1ccc(C(C)(O)c2cccs2)c(OC)c1]

3 M methylmagnesium bromide solution in diethyl ether (10.3 ml; 30.9 mmol; 3.0 eq) is added dropwise to a solution of compound (9) (2.6 g; 10.3 mmol; 1.0 eq) in 100 ml of anhydrous THF cooled to 0° C. The reaction mixture is stirred for 2 hours 0° C. and then 5 ml of 2 M aqueous sodium hydroxide solution and 100 ml of water are added successively. After extraction with ethyl acetate (2×100 ml), the organic phases are combined, dried over $MgSO_4$ and concentrated under reduced pressure to lead to compound (10) (2.7 g; quantitative) obtained as a yellow oil.

$^1$H NMR (300 MHz, $CD_3COCD_3$): δ: 1.78 (s, 3H); 3.59 (s, 3H); 3.67 (s, 3H); 4.79 (s, 1H); 6.39 (dd, 1H); 6.44 (d, 1H); 6.61 (d, 1H); 6.72 (dd, 1H); 7.09 (dd, 1H); 7.27 (d, 1H).

Synthesis of Compound (11)

2-(1-(2,4-dimethoxyphenyl)ethyl)thiophene

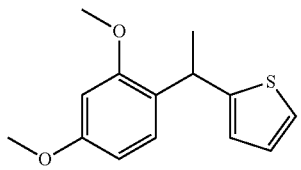 [SMILES: COc1ccc(C(C)c2cccs2)c(OC)c1]

TFA (0.84 ml; 11.3 mmol; 1.1 eq) is added dropwise to a solution of compound (10) (2.7 g; 10.3 mmol; 1.0 eq) and triethylsilane (6.65 ml; 41.2 mmol; 4.0 eq) in 60 ml of anhydrous dichloromethane cooled to 0° C. The reaction mixture is stirred for 2 hours at 0° C. and then 30 ml of saturated aqueous NaHCO$_3$ and 100 ml of water are added successively. The phases are separated and the aqueous phase is extracted with dichloromethane (100 ml). The organic phases are combined, dried over MgSO$_4$ and concentrated under reduced pressure to lead to compound (11) (2.4 g; 95%) obtained as a yellow oil.

$^1$H NMR (300 MHz, CD$_3$COCD$_3$): δ: 1.45 (d, 3H); 3.64 (s, 3H); 3.70 (s, 3H); 4.54 (q, 1H); 6.34 (dd, 1H); 6.41 (d, 1H); 6.71 (dd, 1H); 6.77 (dd, 1H); 6.92 (d, 1H); 7.07 (dd, 1H).

Synthesis of Compound 1

4-(1-(thiophene-2-yl)ethyl)benzene-1,3-diol

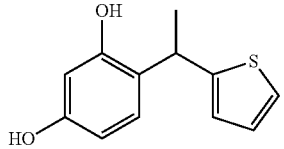

A mixture of compound (11) (1.0 g; 4.0 mmol; 1.0 eq) and pyridinium hydrochloride (30 g) is heated at 200° C. for 1.5 hours. After the mixture cools to room temperature, water (150 ml), ethyl acetate (75 ml) and 2 M aqueous HCl solution (50 ml) are added. The phases are separated and the aqueous phase is extracted with ethyl acetate (2×100 ml). The organic phases are combined, dried over MgSO$_4$ and concentrated under reduced pressure. The residue is purified by chromatography on silica gel (eluent: cyclohexane/ethyl acetate: 8:2; three passes through the column are necessary to obtain an acceptable purity) to lead to compound 1 (0.33 g; 37%) obtained as a beige oil.

$^1$H NMR (300 MHz, DMSO): δ: 1.51 (d, 3H); 4.54 (q, 1H); 6.16 (m, 1H); 6.27 (d, 1H); 6.81 (m, 2H); 6.90 (dd, 1H); 7.27 (dd, 1H); 9.05 (s, 1H); 9.28 (s, 1H).

$^{13}$C NMR (300 MHz, DMSO): δ: 22.16; 32.06; 102.37; 106.29; 123.08; 126.40; 127.67; 129.76; 151.34; 154.84; 156.47; 158.45.

MS (EI): 204.9; 219.94; 221.01

EXAMPLE 2

Synthesis of Compound 2: 4-(1-(pyridin-2-yl)ethyl)benzene-1,3-diol

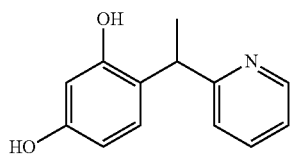

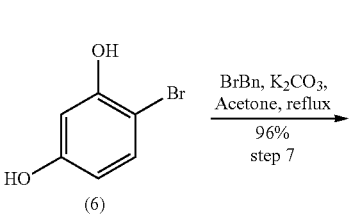

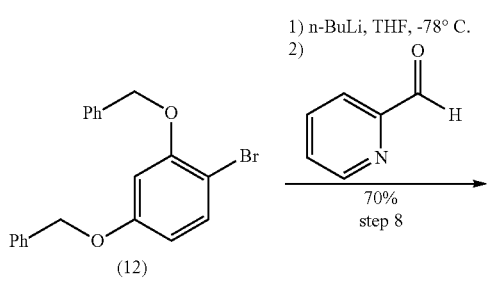

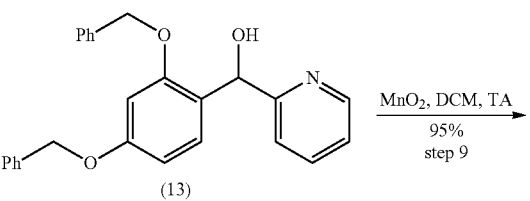

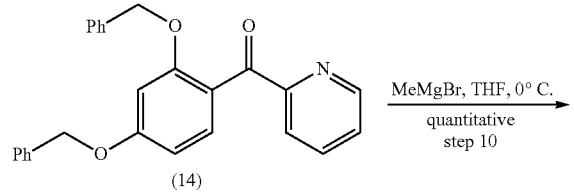

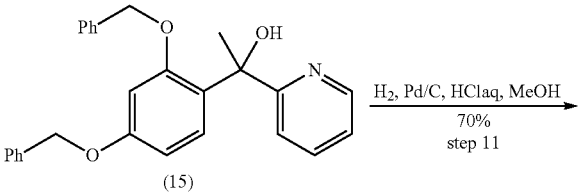

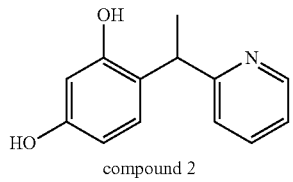

compound 2

Synthesis of Compound (12)

(4-bromo-1,3-phenylene)bis(oxy)bis(methylene)dibenzene

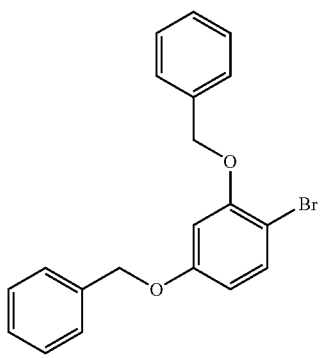 [SMILES: Brc1ccc(OCc2ccccc2)cc1OCc1ccccc1]

Potassium carbonate (11 g; 79.5 mmol; 3.0 eq) and benzyl bromide (9.5 ml; 79.5 mmol; 3.0 eq) are added successively to a solution of compound (6) (5 g; 26.5 mmol; 1.0 eq) in 100 ml of acetone. The reaction mixture is stirred at reflux for 20 hours and then evaporated under reduced pressure. The residue obtained is taken up in 100 ml of water and extracted with ethyl acetate (2×100 ml). The organic phases are combined, dried over $MgSO_4$ and then evaporated. The oil obtained is purified by chromatography on silica gel (eluent: cyclohexane/ethyl acetate: 10:0 then 9:1) to lead to compound (12) (9.4 g; 96%) obtained as a white solid.

$^1$H NMR (300 MHz, $CDCl_3$): δ: 4.95 (s, 2H); 5.06 (s, 2H); 6.43 (dd, 1H); 6.55 (d, 1H); 7.21-7.40 (m, 11H).

Synthesis of Compound (13)

(2,4-bis(benzyloxy)phenyl)(pyridin-2-yl)methanol

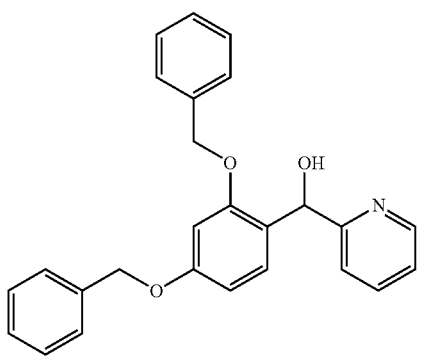 [SMILES: OC(c1ccccn1)c1ccc(OCc2ccccc2)cc1OCc1ccccc1]

1.6 M n-butyllithium solution in hexane (9.3 ml; 14.9 mmol; 1.1 eq) is added dropwise to a solution of compound (12) (5 g; 13.5 mmol; 1.0 eq) in 130 ml of anhydrous THF cooled to −78° C. The solution is stirred for 1 hour at −78° C. and then 2-formylpyridine (4.5 ml; 47.3 mmol; 3.5 eq) is added dropwise. The solution is stirred for 3 hours at −78° C., then for 15 hours at room temperature, and then 800 ml of water is added. The precipitate obtained is filtered using a Buchner funnel, dried under vacuum and then purified by chromatography on silica gel (eluent: cyclohexane/ethyl acetate: 7:3) to lead to compound (13) (3.65 g; 70%) obtained as a beige solid.

$^1$H NMR (300 MHz, $CD_3COCD_3$): δ: 5.13 (m, 3H); 5.16 (s, 2H); 6.16 (d, 1H); 6.61 (dd, 1H); 6.76 (d, 1H); 7.27-7.47 (m, 13H); 7.70 (ddd, 1H); 8.51 (d, 1H).

Synthesis of Compound (14)

(2,4-bis(benzyloxy)phenyl)(pyridin-2-yl)methanone

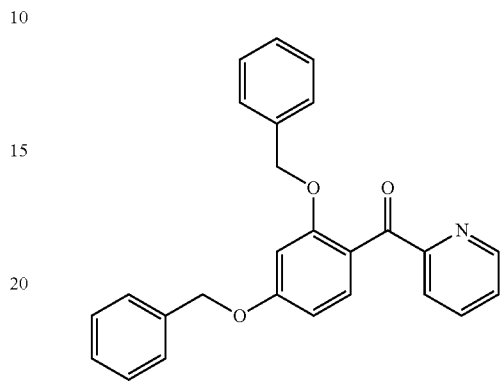

$MnO_2$ (4.9 g; 56.4 mmol; 6.0 eq) is added to a solution of compound (13) (3.6 g; 9.4 mmol; 1.0 eq) in 70 ml of dichloromethane. The reaction mixture is stirred for 4 days at room temperature and then filtered on Celite. The filtrate is concentrated under reduced pressure to lead to compound (14) (3.4 g; 95%) obtained as a white solid.

$^1$H NMR (300 MHz, $CD_3COCD_3$): δ: 5.00 (s, 2H); 5.24 (s, 2H); 6.79 (dd, 2H); 6.84 (s, 2H); 7.21 (m, 3H); 7.43 (m, 7H); 7.83 (dd, 1H); 7.92 (ddd, 1H); 8.56 (dd, 1H).

Synthesis of Compound (15)

1-(2,4-bis(benzyloxy)phenyl)-1-(pyridin-2-yl)ethanol

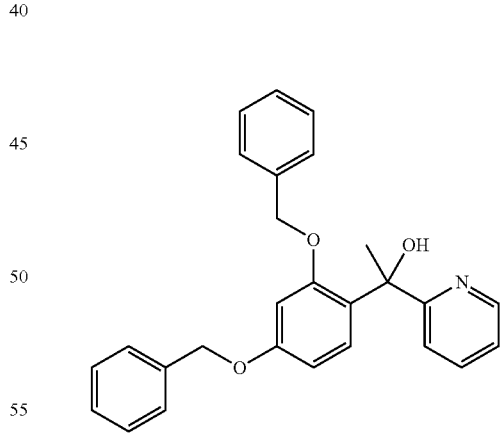

3 M methylmagnesium bromide solution in diethyl ether (8.8 ml; 26.4 mmol; 3.0 eq) is added dropwise to a solution of compound (14) (3.35 g; 8.8 mmol; 1.0 eq) in 70 ml of anhydrous THF cooled to 0° C. The reaction mixture is stirred for 2 hours at 0° C. and then 5 ml of 2 M aqueous sodium hydroxide solution and 100 ml of water are added successively. After extraction with ethyl acetate (2×100 ml), the organic phases are combined, dried over $MgSO_4$ and concentrated under reduced pressure to lead to compound (15) (3.5 g; quantitative) obtained as a white solid.

¹H NMR (300 MHz, CD₃COCD₃): δ: 1.84 (s, 3H); 4.90 (dd ABsyst, 2H); 5.04 (s, 1H); 5.10 (s, 2H); 6.65 (m, 2H); 7.08 (m, 2H); 7.19 (dd, 1H); 7.30-7.43 (m, 9H); 7.47 (m, 2H); 8.39 (dd, 1H).

Synthesis of Compound 2

4-(1-(pyridin-2-yl)ethyl)benzene-1,3-diol

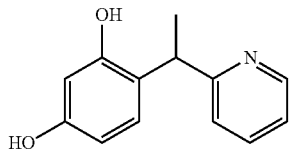 [SMILES: CC(c1ccccn1)c1ccc(O)cc1O]

Pd/C (10%, 50% wet) (1.0 g; 28% by mass) is added to a solution of compound (15) (3.5 g; 8.8 mmol, 1.0 eq) in a methanol/2 M aqueous HCl solution mixture (80 ml/20 ml). The suspension is stirred for 4 days under hydrogen atmosphere and then filtered using a Buchner funnel. The filtrate is evaporated under reduced pressure to lead to a mixture of compound (2) and alkene (28) in the form of hydrochlorides. The residue is dissolved in a methanol/2 M aqueous HCl solution mixture (80 ml/20 ml) and then Pd/C (10%, 50% wet) (1.0 g; 28% by mass) is added. The suspension is stirred for 1 day under hydrogen atmosphere and then filtered using a Buchner funnel. The filtrate is evaporated under reduced pressure. The residue obtained is taken up in saturated aqueous NaHCO₃ solution (100 ml) and then extracted with ethyl acetate (2×150 ml). The organic phases are combined, dried over MgSO₄ and concentrated under reduced pressure. After purification by chromatography on silica gel, compound (2) is obtained as a foam. This foam is taken up in 100 ml of ethanol and then the ethanol is evaporated (operation repeated 3 times) to lead to compound 2 (1.3 g; 70%) obtained as a beige solid.

¹H NMR (300 MHz, DMSO): δ: 1.50 (d, 3H); 4.39 (q, 1H); 6.17 (dd, 1H); 6.26 (d, 1H); 6.88 (d, 1H); 7.16 (m, 2H); 7.65 (ddd, 1H); 8.48 (d, 1H); 9.04 (s, 1H); 9.66 (s, 1H).

¹³C NMR (300 MHz, DMSO): δ: 19.83; 39.4; 102.72; 106.13; 121.11; 121.69; 121.92; 128.39; 136.61; 148.29; 155.40; 156.5; 165.11.

MS (EI): 198.0; 215.0.

EXAMPLE 3

Synthesis of Compound 3: 4-(1-(pyridin-3-yl)ethyl)benzene-1,3-diol

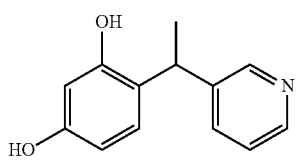

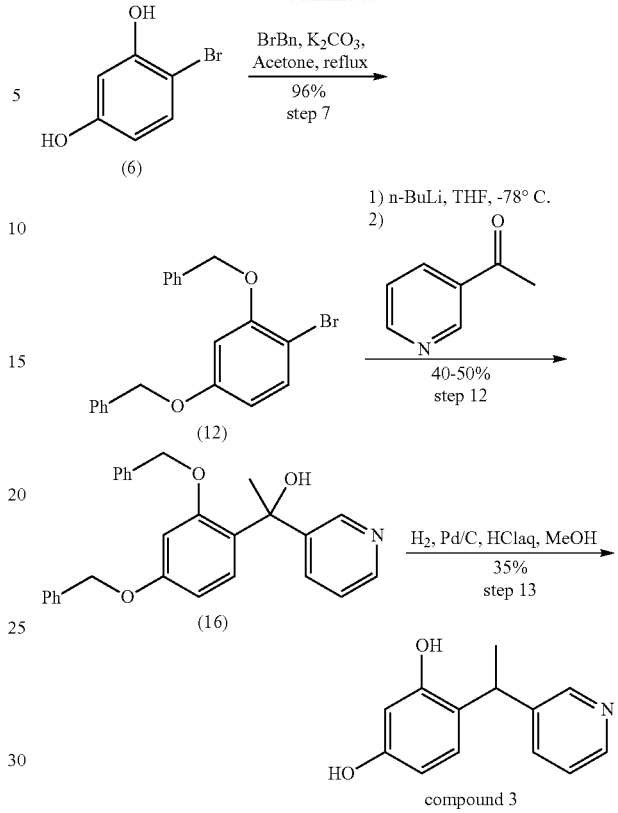

Synthesis of Compound (16)

1-(2,4-bis(benzyloxy)phenyl)-1-(pyridin-3-yl) ethanol

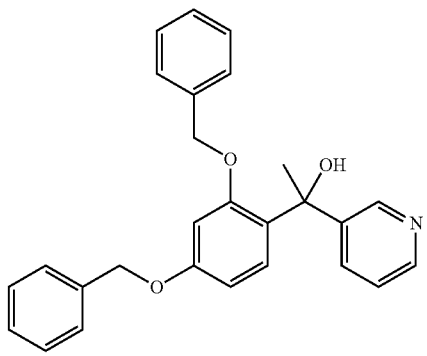 [SMILES: CC(O)(c1cccnc1)c1ccc(OCc2ccccc2)cc1OCc1ccccc1]

1.6 M n-butyllithium solution in hexane (14.9 ml; 23.8 mmol; 1.1 eq) is added dropwise to a solution of compound (12) (8 g; 21.7 mmol; 1.0 eq) in 300 ml of anhydrous THF cooled to −78° C. The solution is stirred for 1 hour at −78° C. and then 3-acetylpyridine (2.6 ml; 23.8 mmol; 1.1 eq) is added dropwise. The solution is stirred for 3 hours at −78° C., then for 15 hours at room temperature, and then 100 ml of water and 50 ml of 2 M aqueous sodium hydroxide solution are added. After extraction with ethyl acetate (2×150 ml), the organic phases are combined, dried over MgSO₄ and concentrated under reduced pressure. The oil obtained is purified by chromatography on silica gel (eluent: cyclohexane/ethyl acetate: 4:6) to lead to a mixture of compound (16) and 3-acetylpyridine (6.7 g; 66% by mass of compound (16); 50%) obtained as a yellow oil.

$^1$H NMR (300 MHz, CD$_3$COCD$_3$): δ: 1.82 (s, 3H); 4.39 (s, 1H); 4.73-4.92 (2d ABsyst, 2H); 5.09 (s, 2H); 6.65 (m, 2H); 6.87 (m, 2H); 7.28-7.44 (m, 9H); 8.25 (dd, 1H); 8.47 (dd, 2H); 8.80 (dd, 1H).

Synthesis of Compound 3

4-(1-(pyridin-3-yl)ethyl)benzene-1,3-diol

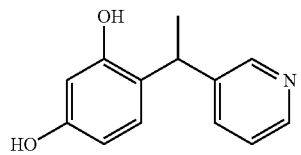

Pd/C (10%, 50% wet) (2 g; 50% by mass) is added to a solution of compound (16) (4 g; 70% by mass; 6.8 mmol, 1.0 eq) in a methanol/1 M aqueous HCl solution mixture (120 ml/40 ml). The suspension is stirred for 4 days under hydrogen atmosphere and then filtered using a Buchner funnel. The filtrate is evaporated under reduced pressure. The oil obtained is taken up in 1 M aqueous sodium hydroxide solution (160 ml) and washed with ethyl acetate (2×80 ml). The aqueous phase is neutralized by adding solid NaH$_2$PO$_4$ and then filtered using a Buchner funnel. The solid obtained is washed thoroughly with water and then dried under strong vacuum to lead to compound 3 (0.5 g; 35%) obtained as a beige solid.

$^1$H NMR (300 MHz, DMSO): δ: 1.48 (d, 3H); 4.31 (q, 1H); 6.18 (dd, 1H); 6.25 (d, 1H); 6.92 (d, 1H); 7.25 (dd, 1H); 7.54 (dd, 1H); 8.32 (ddd, 1H); 8.42 (d, 1H); 9.05 (s, 1H); 9.21 (s, 1H).

$^{13}$C NMR (300 MHz, DMSO): δ: 20.47; 34.36; 102.37; 106.06; 121.87; 123.16; 127.53; 134.47; 142.27; 146.60; 148.95; 155.11; 156.50.

MS (EI): 200.1; 215.1.

EXAMPLE 4

Synthesis of Compound 4:
4-(1-(thiophene-3-yl)ethyl)benzene-1,3-diol

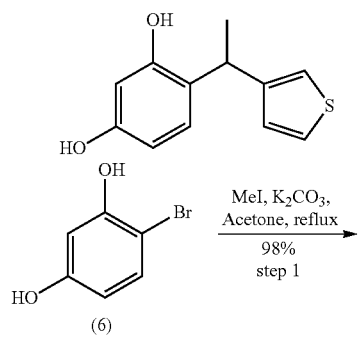

Synthesis of Compound (17)

(2,4-dimethoxyphenyl)(thiophene-3-yl) methanol

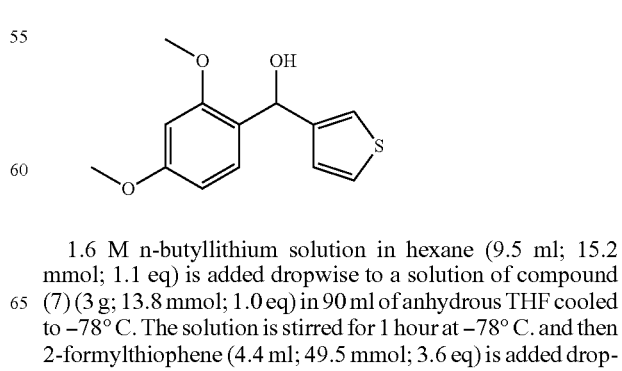

1.6 M n-butyllithium solution in hexane (9.5 ml; 15.2 mmol; 1.1 eq) is added dropwise to a solution of compound (7) (3 g; 13.8 mmol; 1.0 eq) in 90 ml of anhydrous THF cooled to −78° C. The solution is stirred for 1 hour at −78° C. and then 2-formylthiophene (4.4 ml; 49.5 mmol; 3.6 eq) is added drop-

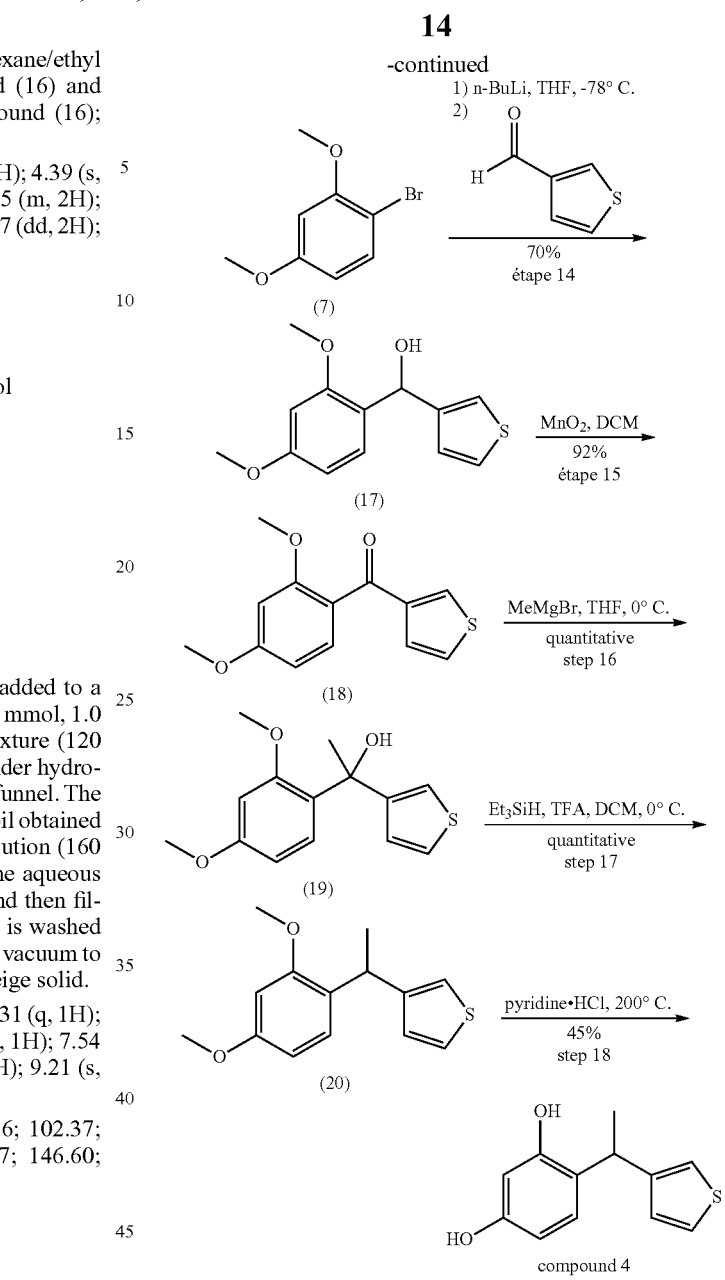

wise. The solution is stirred for 3 hours at −78° C., then for 15 hours at room temperature, and then 150 ml of water is added. After extraction with ethyl acetate (2×150 ml), the organic phases are combined, dried over MgSO₄ and concentrated under reduced pressure. The oil obtained is purified by chromatography on silica gel (eluent: cyclohexane/ethyl acetate: 10:0 to 8:2) to lead to a mixture of compound (17) and thiophene-3-methanol (2.9 g; 83% by mass of compound (17); 70%) obtained as a yellow oil.

¹H NMR (300 MHz, CD₃COCD₃): δ: 3.79 (s, 3H); 3.83 (s, 3H); 4.63 (d, 1H); 6.12 (d, 1H); 6.54 (m, 2H); 7.01 (dd, 1H); 7.19 (dd, 1H); 7.28 (m, 1H).

Synthesis of Compound (18)

(2,4-dimethoxyphenyl)(thiophene-3-yl)methanone

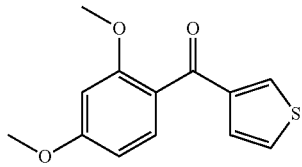 [SMILES: COc1ccc(C(=O)c2ccsc2)c(OC)c1]

MnO₂ (5.0 g; 57.5 mmol; 6.0 eq) is added to a solution of compound (17) (2.9 g (83% by mass); 9.6 mmol; 1.0 eq) in 100 ml of dichloromethane. The reaction mixture is stirred for 2 days at room temperature and then filtered on Celite. The filtrate is concentrated under reduced pressure to lead to a mixture of compound (17) and compound (18). This mixture is reacted under the same conditions for 2 days. After filtration on Celite and evaporation to dryness, the residue is purified by chromatography on silica gel (eluent: cyclohexane/ethyl acetate: 1:0 to 9:1) to lead to compound (18) (2.7 g; 92%) obtained as a yellow oil.

¹H NMR (300 MHz, CD₃COCD₃): δ: 3.77 (s, 3H); 3.90 (s, 3H); 6.64 (dd, 1H); 6.68 (d, 1H); 7.36 (d, 1H); 7.46 (dd, 1H); 7.51 (dd, 1H); 7.96 (m, 1H).

Synthesis of Compound (19)

1-(2,4-dimethoxyphenyl)-1-(thiophene-3-yl)ethanol

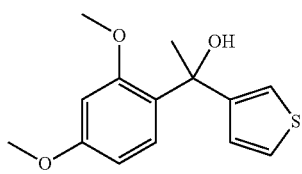 [SMILES: COc1ccc(C(C)(O)c2ccsc2)c(OC)c1]

3 M methylmagnesium bromide solution in diethyl ether (10.5 ml; 31.5 mmol; 3.0 eq) is added dropwise to a solution of compound (18) (2.6 g; 10.5 mmol; 1.0 eq) in 100 ml of anhydrous THF cooled to 0° C. The reaction mixture is stirred for 2 hours at 0° C. and then 5 ml of 2 M aqueous sodium hydroxide solution and 100 ml of water are added successively. After extraction with ethyl acetate (2×100 ml), the organic phases are combined, dried over MgSO₄ and concentrated under reduced pressure to lead to compound (18) (2.8 g; quantitative) obtained as a yellow oil.

¹H NMR (300 MHz, CD₃COCD₃): δ: 1.71 (s, 3H); 3.55 (s, 3H); 3.66 (s, 3H); 4.51 (s, 1H); 6.39 (m, 2H); 6.80 (d, 1H); 6.98 (dd, 1H); 7.12 (dd, 1H); 7.24 (d, 1H).

Synthesis of Compound (20)

3-(1-(2,4-dimethoxyphenyl)ethyl)thiophene

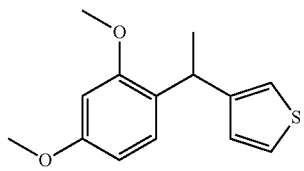 [SMILES: COc1ccc(C(C)c2ccsc2)c(OC)c1]

TFA (0.85 ml; 11.5 mmol; 1.1 eq) is added dropwise to a solution of compound (19) (2.8 g; 10.5 mmol; 1.0 eq) and triethylsilane (6.80 ml; 42.0 mmol; 4.0 eq) in 60 ml of anhydrous dichloromethane cooled to 0° C. The reaction mixture is stirred for 2 hours at 0° C. and then 30 ml of saturated aqueous NaHCO₃ solution and 100 ml of water are added successively. The phases are separated and the aqueous phase is extracted with dichloromethane (100 ml). The organic phases are combined, dried over MgSO₄ and concentrated under reduced pressure to lead to compound (19) (2.6 g; quantitative) obtained as a yellow oil.

¹H NMR (300 MHz, CD₃COCD₃): δ: 1.39 (d, 3H); 3.63 (s, 3H); 3.69 (s, 3H); 4.38 (q, 1H); 6.31 (dd, 1H); 6.40 (d, 1H); 6.76-6.83 (m, 2H); 6.94 (d, 1H); 7.19 (dd, 1H).

Synthesis of Compound 4

4-(1-(thiophene-3-yl)ethyl)benzene-1,3-diol

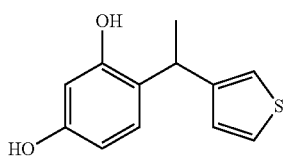

A mixture of compound (20) (1.0 g; 4.0 mmol; 1.0 eq) and pyridinium hydrochloride (30 g) is heated at 200° C. for 1.5 hours. After the mixture cools to room temperature, water (150 ml), ethyl acetate (75 ml) and 2 M aqueous HCl solution (50 ml) are added. The phases are separated and the aqueous phase is extracted with ethyl acetate (2×100 ml). The organic phases are combined, dried over MgSO₄ and concentrated under reduced pressure. The residue is purified by chromatography on silica gel (eluent: cyclohexane/ethyl acetate: 8:2; three passes through the column are necessary to obtain an acceptable purity) to lead to compound 4 (0.4 g; 45%) obtained as a beige oil.

¹H NMR (300 MHz, DMSO): δ: 1.44 (d, 3H); 4.35 (q, 1H); 6.12 (dd, 1H); 6.27 (d, 1H); 6.71 (m, 1H); 6.89 (dd, 1H); 7.08 (dd, 1H); 7.37 (dd, 1H); 8.98 (s, 1H); 9.19 (s, 1H).

¹³C NMR (300 MHz, DMSO): δ: 21.02; 32.11; 102.31; 106.11; 119.32; 123.00; 125.21; 127.68; 128.06; 147.81; 154.84; 156.13.

MS (EI): 204.9; 220.0.

EXAMPLE 5

Synthesis of Compound 5:
4-(1-(thiazol-2-yl)ethyl)benzene-1,3-diol

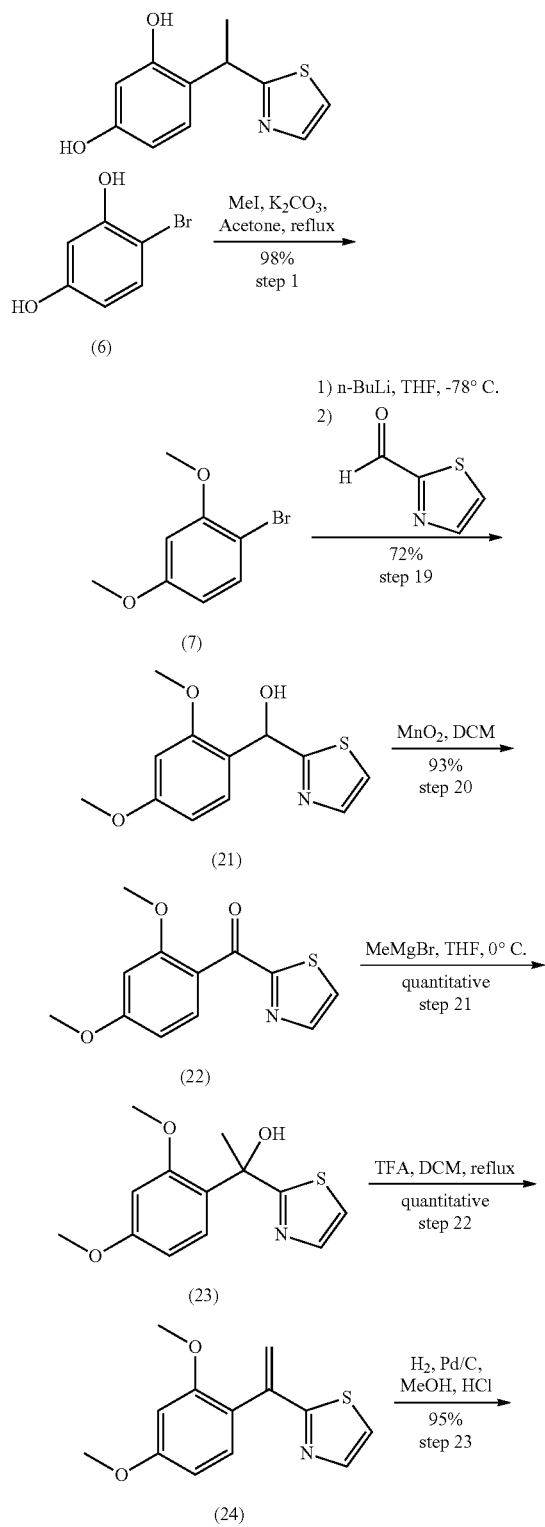

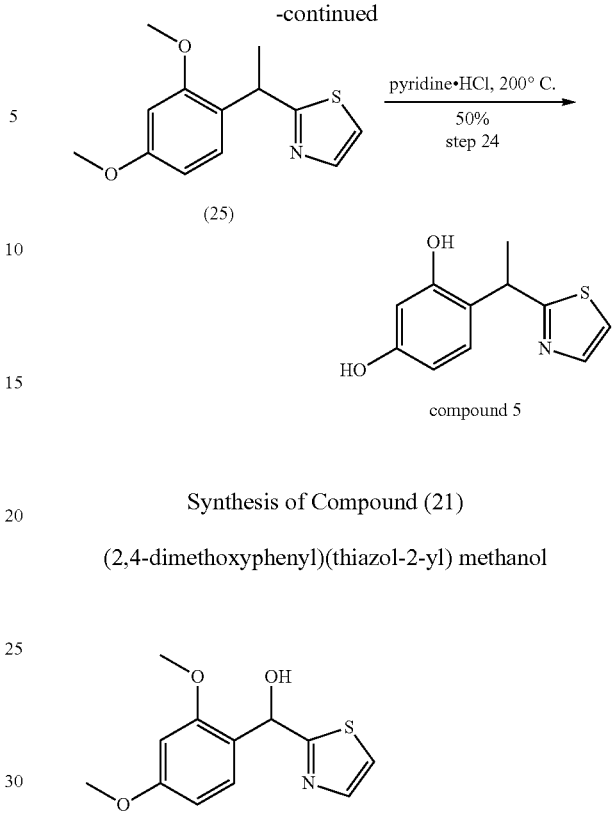

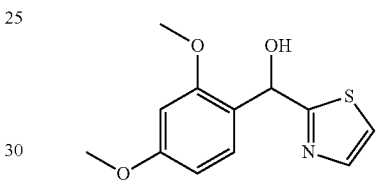

Synthesis of Compound (21)

(2,4-dimethoxyphenyl)(thiazol-2-yl) methanol

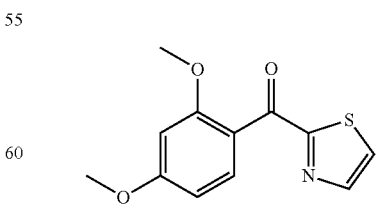

1.6 M n-butyllithium solution in hexane (9.5 ml; 15.2 mmol; 1.1 eq) is added dropwise to a solution of compound (7) (3 g; 13.8 mmol; 1.0 eq) in 90 ml of anhydrous THF cooled to −78° C. The solution is stirred for 1 hour at −78° C. and then 2-formylthiophene (2.4 ml; 37.6 mmol; 2.0 eq) is added dropwise. The solution is stirred for 3 hours at −78° C., then for 15 hours at room temperature, and then 150 ml of water is added. After extraction with ethyl acetate (2×150 ml), the organic phases are combined, dried over MgSO$_4$ and concentrated under reduced pressure. The oil obtained is purified by chromatography on silica gel (eluent: cyclohexane/ethyl acetate: 7:3) to lead to compound (21) (2.5 g; 72%) obtained as a yellow solid.

$^1$H NMR (300 MHz, CD$_3$COCD$_3$): δ: 3.80 (s, 3H); 3.82 (s, 3H); 5.25 (d, 1H); 6.30 (d, 1H); 6.52 (dd, 1H); 6.56 (d, 1H); 7.28 (d, 1H); 7.47 (d, 1H); 7.66 (d, 1H).

Synthesis of Compound (22)

(2,4-dimethoxyphenyl)(thiazol-2-yl)methanone

MnO$_2$ (5.2 g; 59.4 mmol; 6.0 eq) is added to a solution of compound (21) (2.5 g; 9.9 mmol; 1.0 eq) in 100 ml of dichloromethane. The reaction mixture is stirred for 20 hours at room temperature and then filtered on Celite. The filtrate is concentrated under reduced pressure to lead to compound (22) (2.32 g; 93%) obtained as a yellow solid.

¹H NMR (300 MHz, CD₃COCD₃): δ: 3.79 (s, 3H); 3.92 (s, 3H); 6.65 (d, 1H); 6.70 (d, 1H); 7.72 (d, 1H); 8.02 (m, 2H).

Synthesis of Compound (23)

1-(2,4-dimethoxyphenyl)-1-(thiazol-2-yl)ethanol

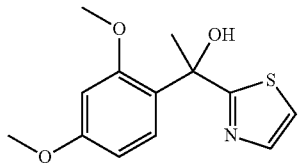 [SMILES: COc1ccc(C(C)(O)c2nccs2)c(OC)c1]

3 M methylmagnesium bromide solution in diethyl ether (9.3 ml; 27.9 mmol; 3.0 eq) is added dropwise to a solution of compound (22) (2.3 g; 9.3 mmol; 1.0 eq) in 100 ml of anhydrous THF cooled to 0° C. The reaction mixture is stirred for 2 hours at 0° C. and then 5 ml of 2 M aqueous sodium hydroxide solution and 100 ml of water are added successively. After extraction with ethyl acetate (2×100 ml), the organic phases are combined, dried over MgSO₄ and concentrated under reduced pressure to lead to compound (23) (2.42 g; quantitative) obtained as a white solid.

¹H NMR (300 MHz, CD₃COCD₃): δ: 1.94 (s, 3H); 3.70 (s, 3H); 3.81 (s, 3H); 5.24 (s, 1H); 6.54 (m, 2H); 7.39 (d, 1H); 7.44 (d, 1H); 7.61 (d, 1H).

Synthesis of Compound (24)

2-(1-(2,4-dimethoxyphenyl)vinyl)thiazole

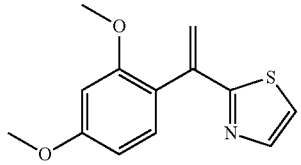 [SMILES: C=C(c1nccs1)c1ccc(OC)cc1OC]

TFA (6.7 ml; 91.0 mmol; 10.0 eq) is added dropwise to a solution of compound (23) (2.4 g; 9.1 mmol; 1.0 eq) in 70 ml of anhydrous dichloromethane. The reaction mixture is stirred for 20 hours at reflux. After the mixture cools to room temperature, 30 ml of saturated aqueous NaHCO₃ and 100 ml of water are added successively. The phases are separated and the aqueous phase is extracted with dichloromethane (100 ml). The organic phases are combined, dried over MgSO₄ and concentrated under reduced pressure to lead to compound (24) (2.5 g; quantitative) obtained as a white solid.

¹H NMR (300 MHz, CD₃COCD₃): δ: 3.69 (s, 3H); 3.86 (s, 3H); 5.32 (s, 1H); 6.22 (d, 1H); 6.58 (dd, 1H); 6.63 (d, 1H); 7.20 (d, 1H); 7.50 (d, 1H); 7.76 (d, 1H).

Synthesis of Compound (25)

2-(1-(2,4-dimethoxyphenyl)ethyl)thiazole

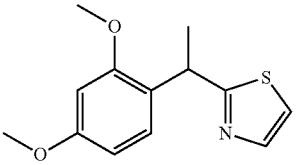 [SMILES: COc1ccc(C(C)c2nccs2)c(OC)c1]

Pd/C (10%, 50% wet) (1.1 g; 50% by mass) is added to a solution of compound (24) (2.2 g; 9.1 mmol, 1.0 eq) in a methanol/1 M aqueous HCl solution mixture (200 ml/40 ml). The suspension is stirred for 4 days under hydrogen atmosphere and then filtered using a Buchner funnel. The filtrate is evaporated under reduced pressure. The oil obtained is taken up in saturated aqueous NaHCO₃ solution (100 ml) and extracted with ethyl acetate (2×80 ml). The organic phases are combined, washed with brine (100 ml), dried over MgSO₄ and concentrated under reduced pressure to lead to compound (25) (2.1 g; 95%) obtained as a beige solid.

¹H NMR (300 MHz, CD₃COCD₃): δ: 1.66 (d, 3H); 3.80 (s, 3H); 3.83 (s, 3H); 4.80 (q, 1H); 6.52 (dd, 1H); 6.57 (d, 1H); 7.19 (d, 1H); 7.37 (d, 1H); 7.66 (d, 1H).

Synthesis of Compound 5

4-(1-(thiazol-2-yl)ethyl)benzene-1,3-diol

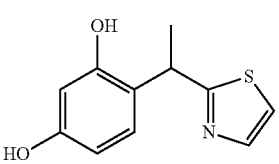

A mixture of compound (25) (1.0 g; 4.0 mmol; 1.0 eq) and pyridinium hydrochloride (30 g) is heated at 200° C. for 1.5 hours. After the mixture cools to room temperature, water (150 ml) and ethyl acetate are added. The phases are separated and the aqueous phase is extracted with ethyl acetate (2×100 ml). The organic phases are combined, washed with brine (100 ml), dried over MgSO₄ and concentrated under reduced pressure. The residue is purified by chromatography on silica gel (eluent: cyclohexane/ethyl acetate: 7:3) to lead to compound (5) (0.45 g; 50%) obtained as a beige solid.

¹H NMR (300 MHz, DMSO): δ: 1.57 (d, 3H); 4.60 (q, 1H); 6.19 (dd, 1H); 6.29 (d, 1H); 6.90 (d, 1H); 7.47 (d, 1H); 7.65 (d, 1H); 9.15 (s, 1H); 9.41 (s, 1H).

¹³C NMR (300 MHz, DMSO): δ: 20.47; 35.54; 102.38; 106.31; 118.91; 120.75; 128.08; 141.77; 155.22; 157.02; 176.15.

MS (EI): 221.0.

Synthesis of Compound (26)

1-(2,4-dimethoxyphenyl)-3-methyl-1-(thiophene-2-yl)butan-1-ol

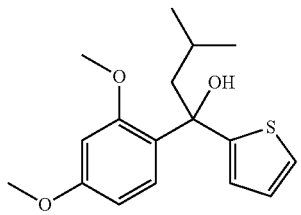 [SMILES: COc1ccc(C(O)(CC(C)C)c2cccs2)c(OC)c1]

2 M isobutylmagnesium bromide solution in diethyl ether (10.3 ml; 30.9 mmol; 3.0 eq) is added dropwise to a solution of compound (9) (2.6 g; 10.3 mmol; 1.0 eq) in 100 ml of anhydrous THF cooled to 0° C. The reaction mixture is stirred for 2 hours at 0° C. and then 5 ml of 2 M aqueous sodium hydroxide solution and 100 ml of water are added successively. After extraction with ethyl acetate (2×100 ml), the organic phases are combined and then dried over $MgSO_4$. The residue is purified by chromatography on silica gel to lead to compound (26) (with a yield of 62%) obtained as a yellow oil.

$^1H$ NMR (300 MHz, $CD_3COCD_3$): δ: 0.67 (d, 3H); 0.77 (d, 3H); 1.59 (m, 1H); 2.46 (dd, 1H); 3.56 (s, 3H); 3.65 (s, 3H); 4.59 (s, 1H); 6.39 (d, 1H); 6.40 (d, 1H); 6.68 (d, 1H); 6.72 (dd, 1H); 7.05 (dd, 1H); 7.37 (d, 1H).

Synthesis of Compound (27)

2-(1-(2,4-dimethoxyphenyl)-3-methylbutyl)thiophene

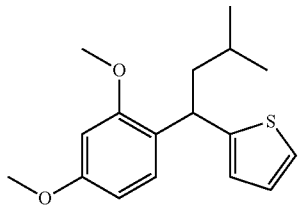 [SMILES: COc1ccc(C(CC(C)C)c2cccs2)c(OC)c1]

Compound 26 (500 mg; 1.63 mmol) is dissolved in dichloromethane (12.5 ml). Triethylsilane (1.04 ml; 6.52 mmol) is added and the solution is cooled to −50° C. TFA (140 µl; 1.1 eq) is added dropwise. The solution is stirred at −50° C. for 2 hours and is allowed to return to room temperature. The solution is stirred overnight. Saturated sodium bicarbonate solution (30 ml) is added, followed by water (30 ml). The phases are separated and the aqueous phase is extracted 3 times with dichloromethane. The organic phases are combined, dried over $Na_2SO_4$, filtered and concentrated. A yellow oil is obtained (480 mg), 100% yield.

$^1H$ NMR (300 MHz, $CD_3COCD_3$): δ: 0.76 (d, 3H); 0.77 (d, 3H); 1.33 (m, 1H); 1.75 (m, 2H); 3.63 (s, 3H); 3.70 (s, 3H); 4.57 (t, 1H); 6.36 (d, 1H); 6.40 (d, 1H); 6.73 (m, 2H); 7.02 (d, 1H); 7.04 (d, 1H).

Synthesis of Compound 28

4-(3-methyl-1-(thiophene-2-yl)butyl)benzene-1,3-diol

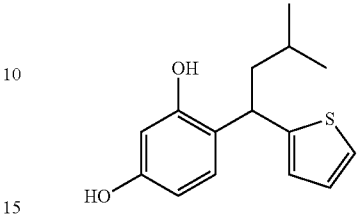

A mixture of compound (11) (1.0 g; 4.0 mmol; 1.0 eq) and pyridinium hydrochloride (30 g) is heated at 200° C. for 1.5 hours. After the mixture cools to room temperature, water (150 ml), ethyl acetate (75 ml) and 2 M aqueous HCl solution (50 ml) are added. The phases are separated and the aqueous phase is extracted with ethyl acetate (2×100 ml). The organic phases are combined, dried over $MgSO_4$ and concentrated under reduced pressure. The residue is purified by chromatography on silica gel (eluent: cyclohexane/ethyl acetate: 8:2; three passes through the column are necessary to obtain an acceptable purity) to lead to compound 28 (with a yield of 20%) obtained as a beige solid.

$^1H$ NMR (300 MHz, $CD_3COCD_3$): δ: 0.90 (d, 3H); 0.92 (d, 3H); 1.51 (m, 1H); 1.83-1.96 (m, 2H); 4.72 (t, 1H); 6.31 (d, 1H); 6.33 (d, 1H); 6.87 (m, 2H); 7.01 (d, 1H); 7.16 (dd, 1H); 8.05 (s, br, 1H); 8.30 (s, br, 1H).

$^{13}C$ NMR (75 MHz, $CD_3COCD_3$): δ: 22.9; 23.5; 27.0; 36.9; 47.2; 103.7; 108.1; 123.8; 124.5; 127.4; 129.7; 152.1; 156.5; 157.8.

MS (ES−): 261

Melting point: 89.9° C.

Synthesis of Compound (29)

1-(2,4-dimethoxyphenyl)-1-(thiophene-2-yl)butan-1-ol

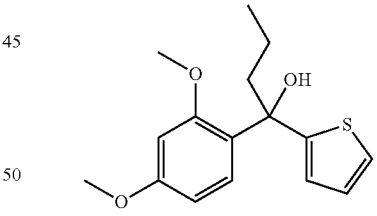

2 M propylmagnesium bromide solution in diethyl ether (10.3 ml; 30.9 mmol; 3.0 eq) is added dropwise to a solution of compound (9) (2.6 g; 10.3 mmol; 1.0 eq) in 100 ml of anhydrous THF cooled to 0° C. The reaction mixture is stirred for 2 hours at 0° C. and then 5 ml of 2 M aqueous sodium hydroxide solution and 100 ml of water are added successively. After extraction with ethyl acetate (2×100 ml), the organic phases are combined and then dried over $MgSO_4$. The residue is purified by chromatography on silica gel to lead to compound (29) (with a yield of 65%) obtained as a light yellow oil.

$^1H$ NMR (300 MHz, $CD_3COCD_3$): δ: 0.89 (t, 3H); 1.30 (m, 2H); 2.10 (td, 1H); 2.52 (td, 1H); 3.71 (s, 3H); 3.80 (s, 3H); 4.83 (s, 1H); 6.52 (d, 1H); 6.56 (d, 1H); 6.80 (d, 1H); 6.88 (dd, 1H); 7.21 (dd, 1H); 7.46 (d, 1H).

Synthesis of Compound (30)

2-(1-(2,4-dimethoxyphenyl)butyl)thiophene

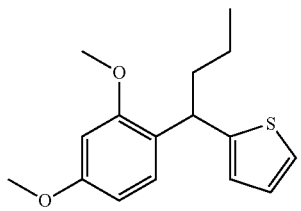 [SMILES: CCCC(c1cccs1)c1ccc(OC)cc1OC]

Compound 26 (500 mg; 1.63 mmol) is dissolved in dichloromethane (12.5 ml). Triethylsilane (1.04 ml; 6.52 mmol) is added and the solution is cooled to −50° C. TFA (140 µl; 1.1 eq) is added dropwise. The solution is stirred at −50° C. for 2 hours and then allowed to return to room temperature. The solution is stirred overnight. Saturated sodium bicarbonate solution (30 ml) is added, followed by water (30 ml). The phases are separated and the aqueous phase is extracted 3 times with dichloromethane. The organic phases are combined, dried over $Na_2SO_4$, filtered and concentrated to obtain compound 27 as a yellow oil.

$^1$H NMR (300 MHz, $CD_3COCD_3$): δ: 0.79 (t, 3H); 1.16 (m, 2H); 1.91 (m, 2H); 3.63 (s, 3H); 3.68 (s, 3H); 4.46 (t, 1H); 6.34 (dd, 1H); 6.39 (d, 1H); 6.73 (m, 2H); 7.03 (m, 2H).

Synthesis of Compound 31

4-(1-(thiophene-2-yl)butyl)benzene-1,3-diol

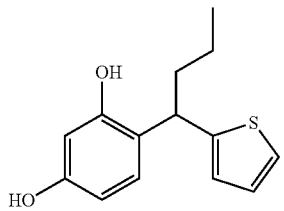

A mixture of compound (11) (1.0 g; 4.0 mmol; 1.0 eq) and pyridinium hydrochloride (30 g) is heated at 200° C. for 1.5 hours. After the mixture cools to room temperature, water (150 ml), ethyl acetate (75 ml) and 2 M aqueous HCl solution (50 ml) are added. The phases are separated and the aqueous phase is extracted with ethyl acetate (2×100 ml). The organic phases are combined, dried over $MgSO_4$ and concentrated under reduced pressure. The residue is purified by chromatography on silica gel (eluent: cyclohexane/ethyl acetate: 8:2; three passes through the column are necessary to obtain an acceptable purity) to lead to compound 31 (with a yield of 18%) obtained as a colorless oil.

$^1$H NMR (300 MHz, $CD_3COCD_3$): δ: 0.78 (t, 3H); 1.17 (m, 2H); 1.88 (m, 2H); 4.47 (t, 1H); 6.19 (dd, 1H); 6.26 (d, 1H); 6.74 (m, 2H); 6.86 (d, 1H); 7.03 (dd, 1H); 7.92 (s, br, 1H); 8.12 (s, br, 1H).

$^{13}$C NMR (75 MHz, $CD_3COCD_3$): δ: 22.9; 23.5; 26.9; 36.9; 47.2; 103.7; 108.1; 123.8; 124.5; 127.4; 129.7; 152.1; 156.5; 157.8.

MS (ES−): [M−H]=247.3.

EXAMPLE 6

Determination of Depigmenting Activity Using an Acellular In Vitro Test: Test of Tyrosinase Inhibition Principle:

This test is used to evaluate the depigmenting activity of the molecules tested.

Tyrosinase is a limiting enzyme in melanogenesis belonging to the family of oxidoreductases. It has in particular the functional groups monophenol monooxygenase (MPMO) and polyphenol oxidase (PPO).

Tyrosinase is synthesized by melanocytes. It is activated during its migration toward keratinocytes via melanosomes. It transforms tyrosine into DOPA and then into dopaquinone, which ultimately leads to polymerization or production of pigments (see diagram below).

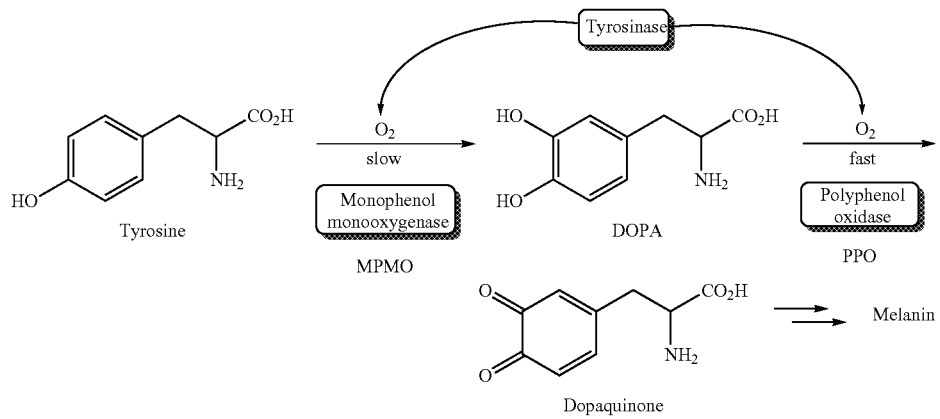

The substrate, L-tyrosine, is transformed by the monophenol monooxygenase functional group into L-DOPA, itself transformed by the tyrosinase's polyphenol oxidase functional group into dopaquinone. The latter will auto-oxidize into dopachrome, which is measured by spectrophotometry at 490 nm.

More precisely, it is global tyrosinase activity (MPMOg) that is measured since ultimately it is dopachrome that is assayed. Thus, the products tested in terms of MPMOg (measurement of activity on PPO and MPMO) can accumulate the inhibition of the 2 functional groups;
- inhibiting only the MPMO functional group in the strict sense (transformation of tyrosine into DOPA) in addition to the PPO test,
- inhibiting only PPO.

General Experimental Conditions:
Reader: Synergy HT program: tyrosinase 280-490 kinetics: kinetics over 45 minutes, reading at t=10 minutes, Tests in transparent 96-well plates, Phosphate buffer (pH 6.8), Enzyme: mushroom tyrosinase (T-3824, Sigma), Substrate: L-tyrosine (T-3754, Sigma), Positive control: Kojic acid (KA) (60890, Fluka) (reference inhibitor).

Reference Molecules for the Test:
Kojic acid: 9 µM<$IC_{50}$<20 µM (PPO), 3 µM<$IC_{50}$<7 µM (MPMO)
Vitamin C: 20 µM<$IC_{50}$<40 µM (PPO)
Reduced glutathione: 55% inhibition at 25 µM (PPO), $IC_{50}$=1-2 µM (MPMO)
Hydroquinone: $IC_{50}$=3-4 µM (MPMO)
Arbutin: 57% inhibition at 88 µM (MPMO)

These exogenous molecules are known to negatively regulate melanogenesis. Hydroquinone inhibits the synthesis of melanin by acting as a substrate of tyrosinase in order to divert its activity. Arbutin, which contains hydroquinone, acts in the same way. Kojic acid decreases tyrosinase activity by inhibiting UV-induced hyperpigmentation. Vitamin C inhibits tyrosinase but also acts as a powerful reducer by preventing the coloring of melanin by oxidation. Vitamin A decreases the expression of tyrosinase.

Results:

| Examples | Structure | Results of tyrosinase depigmenting activities ($IC_{50}$ in µM) |
|---|---|---|
| Compound 1 | | 0.09 |
| Compound 2 | | 0.4 |
| Compound 3 | | 0.2 |
| Compound 4 | 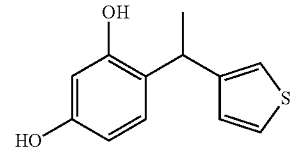 | 0.08 |
| Compound 5 | 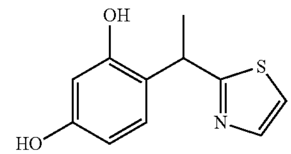 | 1.5 |
| Kojic acid | 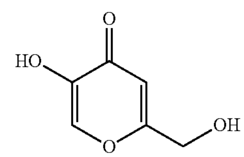 | 15 |
| 4-Butyl-resorcinol | 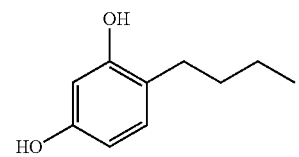 | 1 |
| Arbutin | 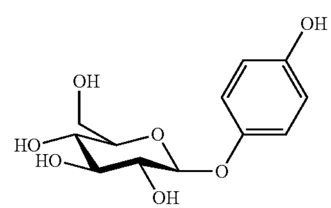 | 90 |
| Unigen resorcinol derivative | | 2 |
| Unigen resorcinol derivative | | 4.9 |
| 4-(1-phenylethyl)benzene-1,3-diol | 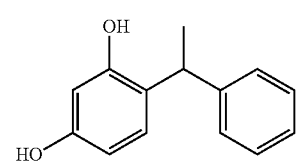 [SMILES: CC(c1ccccc1)c1ccc(O)cc1O] | 0.1 |

The comparative tests carried out on the Unigen compounds of the prior art (WO2010/011630) made it possible to show the superiority of the activity of the compounds in accordance with the invention. More particularly, we can note that compound 3 in accordance with the invention, the closest chemically, has a significantly lower $IC_{50}$ (0.2 μM versus 2 and 4.9 μM).

In relation to the compound 4-(1-phenylethyl)benzene-1,3-diol of the prior art, even if the structures of the compounds in accordance with the invention may seem rather similar (see compound 3), the fact of having a pyridine unit in the place of a phenyl makes it possible to be able to dissolve the active ingredient in aqueous acidic solution, whereas the compound 4-(1-phenylethyl)benzene-1,3-diol) is insoluble in aqueous phase.

Here we have a potential non-negligible aide in formulating the active ingredient in accordance with the invention in salt form; or during the purification of the active agent itself as used during its synthesis (see example 3: synthesis of compound 3).

EXAMPLE 7

Assay of Melanin in B16-F10 Cells

Principle:

This test measures melanin synthesis using a colorimetric assay on a murine melanoma cell line: B16-F10. This test makes it possible to evaluate the depigmenting ability of active ingredients such as kojic acid or arbutin.

B16-F10 cells are seeded in 96-well plates in DMEM medium supplemented with fetal calf serum (FCS) and then incubated for 24 hours at 37° C., 5% $CO_2$. The cells are then stimulated with 0.1 μM α-MSH (to stimulate melanin synthesis; stimulation observed is about 150%) and treated for 72 hours with the active agents to be tested. Each concentration of active agent is tested at least in triplicate. Total melanin and then intracellular melanin dissolved in the lysis buffer are assayed by reading absorbance at 405 nm. The total proteins are assayed in the lysate and the results are expressed in mg melanin/mg proteins: The percentage of activity is calculated as follows:

$$\% \text{ of activity} = \frac{\text{Normalized average of the treated}}{\text{Normalized average of the control}} \times 100$$

A negative value indicates inhibition, whereas a positive value indicates induction of melanin synthesis.

General Experimental Conditions:

Materials:

Cell incubator with $CO_2$ (Heraeus), Oven, Centrifuge (Heraeus), Laminar flow hood, Transparent 96-flat bottomed well plates—Falcon, Sterile cones (Treff Lab, Polylabo, Mithras LB940 (Berthold Technologies)-154/MIPA/003

Biological Material:

B16-F10 cell line between P10 and P20 (murine melanocytes) (ATCC, CRL-6475)

Reagents:

DMEM without phenol red (GIBCOBRL, 31053-028), 200 mM Glutamax-I Supplement (GIBCOBRL, 35050-038), D-PBS (GIBCOBRL, 14190-094), Fetal calf serum (INVITROGEN, 10270-098), Trypsin-EDTA (GIBCOBRL, 25300-054), NaOH (Sigma, S8045-500G), DMSO (Sigma, 471267-14 Nle, Phe-Melanocyte stimulating hormone (Sigma, M-8764), Melanin (Sigma, M-0418), BCA-COPPER(SIGMA, B9643 and C2284), BSA (SIGMA, P0914)

Results:

| Example | Structure | Melanin assay, in strains B16F10 (%) |
|---|---|---|
| Compound 1 | 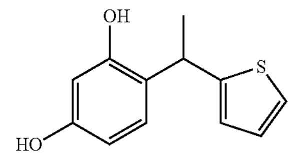 | −50% at 20 μM |
| Compound 2 | 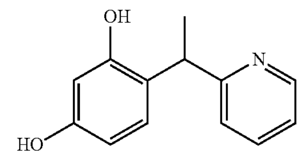 [SMILES: CC(c1ccccn1)c1ccc(O)cc1O] | −26% at 20 μM |
| Compound 3 | 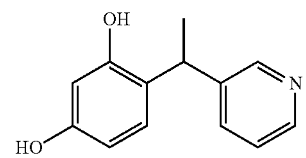 [SMILES: CC(c1cccnc1)c1ccc(O)cc1O] | −52% at 20 μM |
| Compound 4 | 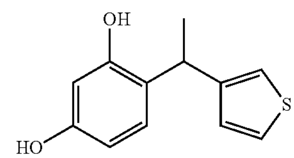 | −52% at 20 μM |
| Compound 5 | 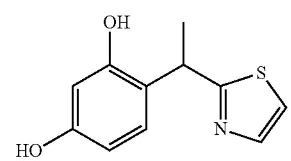 | −33% at 20 μM |
| Compound 28 | 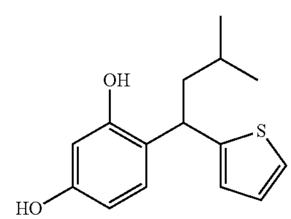 [SMILES: CC(C)CC(c1cccs1)c1ccc(O)cc1O] | −52% at 10 μM |
| Compound 31 | 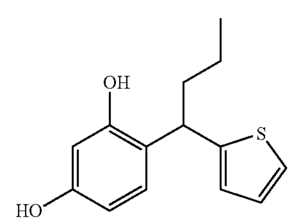 [SMILES: CCCC(c1cccs1)c1ccc(O)cc1O] | −50% at 10 μM |
| Kojic acid | 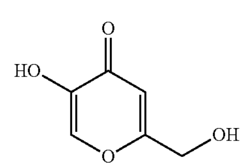 | $IC_{50} = 2400$ μM |

| Example | Structure | Melanin assay, in strains B16F10 (%) |
|---|---|---|
| Arbutin | (structure) | $IC_{50}$ = 158 μM |

It seems important to specify that negative percentage values indicate inhibition of melanin synthesis and, conversely, positive values indicate induction of the latter.

Compounds 1 to 5, 28 and 31 thus prove to be strong inhibitors of melanin synthesis in defined strains of the B16F10 type.

EXAMPLE 8

Test to Study Antioxidant Ability Using Chemiluminescence (Photochem, Analytik Jena)

Principle:

This test is used to determine the antioxidant ability of the molecules. It is a method that generates free radicals by a photochemical signal. The intensity of the oxidation is 1000 times greater than that obtained under normal conditions.

Detection is by chemiluminescence. It enables the evaluation of water-soluble and lipid-soluble antioxidant molecules or extracts.

The results are expressed as equivalents of vitamin C or Trolox (6-hydroxy-2,5,7,8-tetramethylchroman-2-carboxylic acid), respectively. The sensitivity is on the order of the nanomole.

The antioxidant activity studied in this test represents the ability to specifically trap superoxide anions by chemiluminescence.

The quantified results are expressed in Trolox equivalents (standard), or "μg of product for 1 μg of Trolox." This means that a quantity x of sample is needed to obtain activity equivalent to the activity detected for 1 μg of the standard. This represents antioxidant ability relative to a reference, which frees us from concern about the concentration tested.

Generation of Oxygen-Centered Free Radicals:

The superoxide radical ($O_2^{\circ-}$) is generated by a photochemical reaction:

$$L + h\nu(UV) + O_2 \rightarrow L^*O_2 \rightarrow L^{\circ+} + O_2^{\circ-}$$

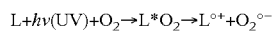

L*: luminol in the excited state
L°+: luminol radical

Signal Detection:

Some of the superoxide anions are quenched by the antioxidants. The remaining free radicals are quantified by chemiluminescence.

$$L^{\circ+} + O_2^{\circ-} \rightarrow N_2 + AP^{*2-} \rightarrow AP^{2-} + h\nu \text{ (luminescence)}$$

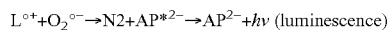

$AP^{*2-}$: aminophthalate in the excited state

| Name | Conditions | Photosensitizing | Antioxidant |
|---|---|---|---|
| Blank | 100% $O_2^{\circ-}$ generated | + | — |
| Standards | Standard range: 1 to 3 nmol | + | Vitamin C or Trolox |
| Test | ±$O_2^{\circ-}$ generated | + | Molecule x to be tested |

The scale used to interpret the results is as follows:

| Products | μg of sample for 1 μg of Trolox | Activity |
|---|---|---|
| Vitamin C | 0.1 to 3.0 | Very good |
| BHT | 3.01 to 50 | Good |
| Cysteine | 50.1 to 1000 | Average |
| Albumin | >1000 | Weak |
| Lipoic acid | NEGATIVE | None |

The majority of the compounds have results comparable to vitamin C. All of the compounds show results below 1000 μg of Trolox (301 μg being the weakest result obtained with resorcinol sulfone); thus, they all have an advantageous antioxidant activity.

Results:

| Example | Structure | μg of sample for 1 μg of Trolox |
|---|---|---|
| Compound 1 | (structure) | 13.7 |
| Compound 2 | (structure) | 10.4 |
| Compound 3 | (structure) | 8.7 |
| Compound 4 | (structure) | 15.4 |
| Compound 5 | (structure) | 11.7 |

EXAMPLE 9

Depigmenting Composition

| Ingredients (trade names) | INCI designation | Percentage by weight | Function |
|---|---|---|---|
| I. Purified water | water | qs 100% | |
| Hydrolite 5 | Pentylene Glycol | 3 | Humectant, Preservative |
| EDTA, 2Na | Disodium EDTA | 0.1 | Sequestering agent |
| Microcare PM4 | Phenoxyethanol-Paraben | 0.8 | Preservatives |
| Water-soluble PCL | Trideceth-9 & PEG-5 Ethylhexanoate | 1.5 | Aqueous emollient |
| II. Pemulen TR-1 | Acrylates/C10-30 Alkyl Crosspolymer | 0.5 | Gelling agent, stabilizer |
| III. Stearin TP | Stearic acid | 2 | Emulsifier, consistency factor |
| Liquid PCL | Cetearylethylhexanoate & Isopropylmyristate | 3 | Emollient |
| DC200 | Dimethicone | 0.3 | Emollient |
| Myritol 318 | Capric or caprylic triglycerides | 3 | Emollient |
| Primol 352 | Liquid paraffin | 2 | Emollient |
| IV. Depigmenting active agent | Choice of compounds 1 to 5 | 0.5 | Active agent |
| V. Sodium hydroxide | NaOH | 0.08 | pH adjuster |

In such a composition, the percentage of the active ingredient can vary between 0.01% and 10% by weight and preferably from 0.1% to 5% by weight in relation to the total weight of the composition.

The invention also relates to pharmaceutical or cosmetic compositions including at least one of the compounds of formula (I) in combination with at least one pharmaceutically or cosmetically acceptable excipient In accordance with a particular embodiment of the invention, the pharmaceutical or cosmetic compositions include at least one of the compounds of formula (I) in combination with at least one pharmaceutically or cosmetically acceptable excipient and a fatty phase.

In accordance with a particular embodiment of the invention, the pharmaceutical or cosmetic compositions include at least one of the compounds of formula (I) in combination with at least one pharmaceutically or cosmetically acceptable excipient and an emollient.

The present invention relates to a cosmetic depigmenting composition for the skin and/or head hair and/or body hair characterized in that it includes at least one compound of formula (I).

The invention also relates to a cosmetic anti-aging composition for the skin, characterized in that it includes at least one compound of formula (I).

The composition in accordance with the invention can further include conventional cosmetic adjuvants notably selected from fatty phases, organic solvents, thickeners, softeners, opacifiers, stabilizers, emollients, anti-foaming agents, hydrating agents, fragrances, preservatives such as parabens, polymers, loads, sequestering agents, bactericides, odor absorbers, alkalizing or acidifying agents, surfactants, anti-free radicals, antioxidants, vitamins E and C, α-hydroxyacids, or thermal spring water or any other ingredient commonly used in cosmetics, in particular for the manufacture of compositions of this type.

The composition in accordance with the invention can further include a fatty phase. The fatty phase can be constituted by an oil or a wax or mixtures thereof, and can further include fatty acids, fatty alcohols and fatty acid esters. The oils can be selected from animal, plant, mineral or synthetic oils and notably from vaseline oil, paraffin oil, silicone oils, volatile or not such as dimethicone; isoparaffins, polyolefins, fluorinated and perfluorinated oils. Similarly, the waxes can be selected from animal, fossil, plant or synthetic waxes such as beeswaxes, candelilla waxes, carnauba waxes, shea butter, petroleum wax (or microcrystalline wax), paraffin, and mixtures thereof.

The composition in accordance with the invention can further include a polyol miscible with water at room temperature (about 25° C.), notably selected from polyols having notably from 2 to 20 carbon atoms, preferably having from 2 to 10 carbon atoms, and preferentially having from 2 to 6 carbon atoms, such as glycerin; glycol derivatives such as propylene glycol, butylene glycol, pentylene glycol, hexylene glycol, dipropylene glycol, diethylene glycol; glycol ethers such as $C_1$-$C_4$ alkyl ethers of mono-, di- or tri-propylene glycol, $C_1$-$C_4$ alkyl ethers of mono-, di- or tri-ethylene glycol; and mixtures thereof.

The composition in accordance with the invention can also include thickening agents or rheology modification agents such as, for example, nonionic hydrophobically modified ethoxylated urethanes, polycarboxylic acid thickeners such as copolymers of acrylates/steareth-20 methacrylate, carbomers, crosslinked acrylate copolymers and mixtures thereof.

The composition in accordance with the invention can also include acids and bases making it possible to adjust the pH range of said composition. The bases can be inorganic (sodium hydroxide, potassium hydroxide, aqueous ammonia, etc.) or organic such as mono-, di- or tri-ethanolamine, aminomethylpropanediol, N-methyl-glucamine, basic amino acids such as arginine and lysine, and mixtures thereof.

The composition in accordance with the invention can also include skin conditioning agents. Examples of skin conditioning agents include, but are not limited to, anionic, cationic and nonionic emulsifiers such as sodium lauryl sulfate, sodium dioctyl sulfosuccinate, sodium stearate, sorbitan ester; ethoxylated fatty acids; ethoxylated fatty alcohols such as trideceth-9 and PEG-5 ethylhexanoate; stearic acid; and any other emulsifier and conditioning agent known to persons skilled in the art; and mixtures thereof.

The composition in accordance with the invention can further contain other active ingredients leading to a complementary effect.

The composition in accordance with the invention can be provided in any form suitable for topical application, in particular on the skin and/or hair. In particular, they can be provided as emulsions obtained by the dispersion of a fatty phase in an aqueous phase, for example an oil-in-water or water-in-oil or multiple emulsion, or as a gel or a liquid, paste or solid anhydrous product, or as a dispersion in the presence of spherules. The composition in accordance with the invention can also be less fluid and can be provided as a white or colored cream, an ointment, a milk, a lotion, a serum, a paste, a mask, a powder, a solid stick or, optionally, an aerosol, a foam or a spray.

The invention claimed is:
1. A compound of general formula (I)

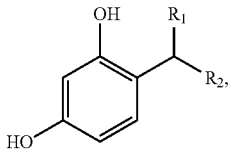

wherein:
R$_1$ is a C$_1$-C$_4$ alkyl group, and
R$_2$ is a nitrogen-, sulfur- or oxygen-containing heteroaromatic ring, optionally substituted by a linear or branched C$_1$-C$_4$ alkyl radical.

2. The compound in accordance with claim 1, wherein R$_1$ is a methyl group.

3. The compound in accordance with claim 1, wherein R$_2$ is a heteroaromatic single-ring, preferably with 5 or 6 members.

4. The compound in accordance with claim 1, wherein R$_2$ is selected from the group consisting of a pyridine, thiophene and thiazole heterocycle.

5. The compound in accordance with claim 1, wherein R$_1$ is a methyl group and R$_2$ is selected from the group consisting of 3-pyridyl, 4-pyridyl, 2-furyl, 3-furyl, 2-thiophenyl, 3-thiophenyl, and 2-thiazolyl.

6. The compound in accordance with claim 1, wherein the compound is selected from one of the following compounds:
4-(1-(pyridin-2-yl)ethyl)benzene-1,3-diol;
4-(1-(pyridin-3-yl)ethyl)benzene-1,3-diol;
4-(1-(pyridin-4-yl)ethyl)benzene-1,3-diol;
4-(1-(thiophene-2-yl)ethyl)benzene-1,3-diol;
4-(1-(thiophene-3-yl)ethyl)benzene-1,3-diol;
4-(1-(thiazol-2-yl)ethyl)benzene-1,3-diol;
4-(1-(1-methyl-1H-benzo[d]imidazol-2-yl)ethyl)benzene-1,3-diol;
4-(1-(1-methyl-1H-indol-2-yl)ethyl)benzene-1,3-diol;
4-(1-(benzo[b]thiophene-2-yl)ethyl)benzene-1,3-diol;
4-(1-(thiophene-2-yl)butyl)benzene-1,3-diol; and
4-(3-methyl-1-(thiophene-2-yl)butyl)benzene-1,3-diol.

7. A compound as defined in accordance with claim 1, suitable for use as a cosmetic active ingredient.

8. A compound as defined in accordance with claim 1, suitable for use as a drug.

9. A compound as defined in accordance with claim 1, suitable for use as a depigmenting active ingredient.

10. A compound as defined in accordance with claim 1, suitable for use as an antioxidant active ingredient.

11. A pharmaceutical or cosmetic composition, wherein the composition comprises as an active ingredient at least one compound of claim 1 in combination with a pharmaceutically or cosmetically acceptable excipient.

12. The pharmaceutical or cosmetic composition in accordance with claim 11, the wherein a quantity of compound of claim 1 varies between 0.01% and 10% by weight in relation to the total weight of the composition.

13. The cosmetic composition in accordance with claim 11, suitable for use in depigmenting the skin and/or head hair and/or body hair.

14. The cosmetic composition in accordance with claim 11, suitable for use as a skin anti-aging product.

15. The pharmaceutical composition in accordance with claim 11, suitable for use in disinfecting the skin.

16. A method of cosmetic treatment and/or prevention of aging of the skin, comprising the application on the skin of a cosmetic composition comprising at least one compound of claim 1.

17. A method of bleaching and/or lightening human skin and/or body hair and/or head hair, comprising the application on the skin and/or body hair and/or head hair of a cosmetic composition comprising at least one compound of claim 1.

18. The compound of claim 1, wherein the heteroaromatic ring is substituted by a methyl radical.

19. The compound in accordance with claim 18, wherein R$_1$ is a methyl group.

* * * * *